(12) United States Patent
Braun (10) Patent No.: US 12,343,018 B2
(45) Date of Patent: Jul. 1, 2025

(54) TISSUE CLIP APPLICATION FITTING OR RETROFITTING SET

(71) Applicant: Ovesco Endoscopy AG, Tübingen (DE)

(72) Inventor: Marcus Braun, Weil im Schönbuch (DE)

(73) Assignee: Ovesco Endoscopy AG (DE)

( * ) Notice: Subject to any disclaimer, the term of this patent is extended or adjusted under 35 U.S.C. 154(b) by 416 days.

(21) Appl. No.: 17/925,511

(22) PCT Filed: May 11, 2021

(86) PCT No.: PCT/EP2021/062504
§ 371 (c)(1),
(2) Date: Nov. 15, 2022

(87) PCT Pub. No.: WO2021/233740
PCT Pub. Date: Nov. 25, 2021

(65) Prior Publication Data
US 2023/0181194 A1    Jun. 15, 2023

(30) Foreign Application Priority Data

May 19, 2020    (DE) .................... 10 2020 113 535.1

(51) Int. Cl.
*A61B 17/128*    (2006.01)
*A61B 1/00*    (2006.01)

(52) U.S. Cl.
CPC ...... *A61B 17/1285* (2013.01); *A61B 1/00137* (2013.01)

(58) Field of Classification Search
CPC .......... A61B 2017/00296; A61B 17/10; A61B 17/12; A61B 17/128; A61B 17/1285;
(Continued)

(56) References Cited

U.S. PATENT DOCUMENTS

| 5,398,844 A | 3/1995 | Zaslavsky et al. |
| 8,721,528 B2 | 5/2014 | Ho et al. |

(Continued)

FOREIGN PATENT DOCUMENTS

| DE | 2447055 A1 | 4/1976 |
| DE | 8122103 U1 | 10/1986 |

(Continued)

OTHER PUBLICATIONS

Office Action (Notice of Reasons for Refusal) issued Oct. 29, 2024, by the Japanese Patent Office in corresponding Japanese Patent Application No. 2022-571350 and an English translation of the Office Action. (10 pages).

(Continued)

*Primary Examiner* — Katherine M Shi
(74) *Attorney, Agent, or Firm* — Buchanan Ingersoll & Rooney PC (57) ABSTRACT

A tissue clip application fitting or retrofitting set comprising a cap attachment configured to be mounted on the distal end portion of a shaft-type medical endoscope. The cap attachment has a proximal mounting or placement portion and a distal tissue clip holding portion, in the region of which a cavity open at least in the distal direction is formed inside a radially outward-pointing peripheral surface. A tissue clip is supported on the peripheral surface, and can be displaced in the distal direction by a pull-off device in the form of a pull-off ring mounted on the radial outer peripheral surface of the tissue clip holding portion so that it can axially slide and move the tissue clip. The pull-off ring is operated by a cable pull that is in direct contact with the pull-off ring for the transmission of sliding force in at least two coupling or engagement points.

6 Claims, 3 Drawing Sheets

(58) Field of Classification Search
CPC ........ A61B 2017/0023; A61B 1/00137; A61B 17/083; A61B 1/00087; A61B 17/1227
See application file for complete search history.

(56) References Cited

U.S. PATENT DOCUMENTS

| | | |
|---|---|---|
| 2004/0006256 A1 | 1/2004 | Suzuki et al. |
| 2011/0208210 A1 | 8/2011 | Baur et al. |
| 2013/0325039 A1 | 12/2013 | Noda |
| 2021/0052141 A1 | 2/2021 | Schurr et al. |

FOREIGN PATENT DOCUMENTS

| | | |
|---|---|---|
| DE | 202008007774 U1 | 8/2008 |
| DE | 102017112896 A | 12/2018 |
| JP | 2011120884 A1 | 6/2011 |
| WO | 9745060 A1 | 12/1997 |

OTHER PUBLICATIONS

English Translation of the Written Opinion for Application No. PCT/EP2021/062504, dated Aug. 18, 2021, 4 pages.
German Search Report for German Application No. 10 2020 113 535.1, dated Dec. 21, 2020, with partial translation, 11 pages.
International Search Report and Written Opinion for Application No. PCT/EP2021/062504, dated Aug. 18, 2021, 7 pages.

TISSUE CLIP APPLICATION FITTING OR RETROFITTING SET

This application is a U.S. National Phase application of PCT International Application No. PCT/EP2021/062504, filed May 11, 2021, which claims the benefit of DE 10 2020 113 535.1, filed May 19, 2020, both of which are incorporated by reference herein.

The disclosure relates to a tissue-clip application fitting or retrofitting set comprising a cap attachment which is designed to be mounted or slipped/attached on/onto the distal end portion of a medical endoscope of the shaft type and which, for this purpose, has a proximal mounting/placement portion and a distal tissue-clip holding portion, in the region of which a cavity which is open in the distal direction is formed on the inside and on one of the distal tissue-clip holding portion's peripheral surfaces which points radially outwards, a tissue clip is radially supported, which can be displaced in the radial direction via a pull-off device which is preferably operable/actuatable from the proximal end portion of the endoscope or extracorporeally, the pull-off device being in the form of a pull-off ring which is axially slidably mounted on the radial outer peripheral surface of the tissue-clip holding portion and guides/displaces/moves the tissue clip.

BACKGROUND OF THE DISCLOSURE

Endoscopes are generally medical working tools for visual exploration and, if applicable, manipulation of cavities in a patient's body. For exploration, they generally have optical devices at the distal (facing the patient or not facing the user) end of the endoscope (also known as the endoscope head). For manipulation, they optionally have one or more internal working channels extending from a proximal (not facing the patient or facing the user) endoscope portion, which conventionally protrudes outward from the patient cavity, or an extracorporeal endoscope handle, through an adjoining flexible or rigid endoscope shaft to the endoscope head, and allow extracorporeal insertion or feeding of one or more medical instruments, such as forceps, anchors, scissors, needles, slings, knives and the like.

Such endoscopes may optionally be provided with additional capabilities, for example by attaching, radially on the outside at the distal endoscope head, a cap or sleeve on the endoscope head which accommodates/contains at least the optics. Here, the cap or sleeve is provided with certain functions or equipped with certain functional elements. This enables the endoscope, in addition to its original functions, namely exploration and/or as access for minimally invasive (medical) instruments, to be used as a (minimally invasive) instrument itself for performing an interventional or surgical procedure.

PRIOR ART

Endoscopes with additional functions implemented via caps (cap attachments) are already known from the prior art. For example, DE 10 2017 112 896 A1 shows a tissue-clip fitting set or retrofitting set, the cap attachment of which can be attached onto the distal end of an endoscope in order to strip a tissue clip from the cap attachment via a pull-off ring.

Another example of an endoscope cap is disclosed in DE 20 2008 007 774 U1. The endoscope cap has a holding and pull-off device for a tissue clip which can be pushed onto an expanding sleeve of the endoscope cap. A front groove is arranged on the front edge of the expanding sleeve, which opens and slits open the cap jacket wall on both sides. Furthermore, the endoscope cap has a pull-off string or fabric that radially traverses the front groove in an axially frontal cap portion and is slidably inserted or insertable into an endoscope channel for actuation thereof at a radially inner side of the endoscope cap.

Also shown in US 2013/0 325 039 A1 is an endoscope cap that allows a tissue clip to be pulled off via a proximally actuated pull-off device in the form of an actuator cable coupled to a carrier/pull-off ring disposed within the cap and displacing the tissue clip.

However, the endoscope caps disclosed in the prior art always have the disadvantage that pull-off rings guided inside the cap reduce the usable cross-sectional area of the working channel. By contrast, pull-off rings that are guided on the outer peripheral surface and can be actuated with a pull string tend to jam, which in turn can lead to damage.

SUMMARY OF THE DISCLOSURE

The objects and aims of the disclosure are to eliminate or at least reduce the disadvantages of the prior art. In particular, a tissue-clip application fitting or retrofitting set is to be provided which eliminates or reduces the risk of jamming of the pull-off ring without (excessively) restricting the usable area of the working channel.

The objects and aims are solved in accordance with the disclosure with respect to a generic tissue-clip application fitting or retrofitting set by the subject matter of claim 1. The disclosure is thus based on the understanding of a force introduction into the pull-off ring that is as uniform or symmetrical as possible.

According to the disclosure, the tissue-clip application fitting or retrofitting set is configured/adapted so that, when the pull-off device is actuated, an axial force distributed over the circumference of the pull-off ring or applied to the pull-off ring as symmetrically as possible is applied.

For this purpose, according to a first embodiment of the present disclosure, which may be claimed independently, if applicable, the principle of a simple pulley is applied constructively, according to which a (first) cable pull end is held stationarily (distally),
a central portion of the cable pull is longitudinally slidably coupled to the (proximal) load, specifically the pull-off ring, and
another (second) cable pull end is guided back around a distal deflection in the direction of the (proximal) load and if applicable beyond it (in the proximal direction).

The central portion, which is operatively connected to the load, namely the pull-off ring, can thus be dimensioned and/or positioned in such a way that it causes a substantially symmetrical application of force to the load (pull-off ring), thus avoiding jamming. Specifically, the central portion of the cable pull may be in (sliding) contact with the load (the pull-off ring) at at least two (preferably diametrically opposite) hinge sites (connection loop, attachment points) spaced apart in the circumferential direction of the endoscope/the (separate) endoscope cap, so that when the cable pull is pulled, its central portion slides longitudinally at the hinge sites and thereby displaces the pull-off ring in the distal direction according to the pulley principle. Preferably, the cable pull portion between the at least two hinge sites on the pull-off ring is guided longitudinally in the circumferential direction (preferably on its proximal front side), which enables an even more uniform introduction of force into the pull-off ring over the corresponding circumferential portion.

Advantageous embodiments are claimed in the dependent claims and are explained below.

In a preferred embodiment, the axial force can act on the pull-off ring during operation/actuation of the pull-off device, as already indicated above, at at least two hinge sites/engagement points distributed over the circumference, preferably uniformly/evenly. In this context, it may be advantageous if a pull-off string/pull-off fabric/pull-off cable is coupled (looped) to the pull-off ring and is configured to be guided with one end portion from the cavity to the proximal end portion of the endoscope and to be fixed with the other end portion to the tissue-clip holding portion. Particularly preferably, the one pull-off string may be guided on the cap attachment in such a way that when the pull-off string is actuated, it pulls the pull-off ring at the two engagement points in the distal direction, which allows the pull-off ring at the at least two engagement points to be pulled in the distal direction with only a single (non-bifurcated) pull-off string and at the same time ensures a more uniform application of force and thus a lower tilting moment.

According to a particularly advantageous further development, the pull-off string may be guided
- preferably from the proximal end portion of the endoscope through the internal (or external) working channel of the endoscope into the cavity,
- from the cavity (of the separate endoscope cap) via a first distal radial through opening formed in the tissue-clip holding portion to the radial outside,
- then through a first axial through opening formed in the pull-off ring,
- then along the outer peripheral surface of the (separate) endoscope cap and through a second axial through opening formed in the pull-off ring, preferably offset by 180° from the first axial through opening, as well as
- a second distal radial through opening formed in the tissue-clip holding portion, preferably offset by 180° from the first radial through opening, into the cavity, where it may be fixed to the tissue-clip holding portion (fixing site).

Preferably, at least two pull-off strings assigned to the engagement points may be arranged on the pull-off ring. This ensures that substantially the same axial force is applied at each engagement point and that no tilting moment occurs.

It is also conceivable that the pull-off string may be guided along the cap attachment in such a way that more than two engagement points are configured. Here, the pull-off string may be guided through further radial through openings and axial through openings in order to obtain additional engagement points. In particular, a deflection point may be arranged or configured distally between the engagement points, as in a pulley. In a particularly advantageous configuration, the pull-off string may be configured to pass over the front edge inwards into the cavity, through a further, distal radial through opening outwards again and there to the next proximal engagement point on the pull-off ring.

According to a second alternative embodiment of the present disclosure, which may be claimed independently, if applicable, the pull-off ring has a support/bearing element fastened/fixed to the cap attachment, preferably to its tissue-clip holding portion, for example in the form of a support ring with an axial or radial outer surface which has a slope/pitch in the distal direction (e.g. a wedge-shaped distal front side or a spindle) and a sliding ring which is axially slidably and rotatably mounted along the outer peripheral surface of the tissue-clip holding portion and (at least partially) arranged distally of the support element/support ring and the sliding ring has a profiling which is in operative engagement with the slope of the support ring.

Furthermore, the pull-off string is arranged on the sliding ring in such a way that when it is (manually) actuated, it rotates the sliding ring about its axis of rotation and displaces it in the distal direction as a result of the operative engagement of its profiling with the slope of the support ring.

For this purpose, it is advantageous if at least one respective ramp/cam/support wedge is configured on a front surface of the support ring facing the sliding ring and on a front surface of the sliding ring facing the support ring, wherein the wedge directions are opposite to each other, so that the support ring and the sliding ring are being axially spaced apart from each other when the pull-off string is actuated and the sliding ring is correspondingly rotated relative to the support ring.

According to an alternative further development, an internal thread may be configured on the sliding ring and, an external thread with a corresponding pitch may be configured on the support ring, which engages with the internal thread, so that the support ring and the sliding ring are being axially spaced apart when the pull-off string is actuated. Of course, an internal thread may also be configured on the support ring and an external thread engaging with the internal thread may be configured on the sliding ring, so that the support ring and the sliding ring are being axially spaced apart when the pull-off string is actuated.

Furthermore, it may be advantageous if the at least one pull-off string is guided in an axial groove formed in the tissue-clip holding portion in the distal and/or proximal direction, so that the tissue clip passes over the pull-off string guided in the axial groove during stripping.

According to the disclosure, the at least one pull-off string may be guided via a separate longitudinal passage, preferably arranged laterally along the endoscope shaft, to the proximal end portion of the endoscope. However, it is also conceivable that the at least one pull-off string is guided in an internal working channel of the endoscope towards the proximal end portion of the endoscope.

For optimized use of the tissue-clip application fitting or retrofitting set, the cap attachment may be configured with a cap sleeve, which is firmly, preferably in one piece of material, connected to the cap attachment and radially, at least in sections, surrounds the tissue clip mounted on the tissue-clip holding portion.

BRIEF DESCRIPTION OF THE FIGURES

The disclosure is explained in more detail below with the aid of figures based on preferred configuration examples. The following is shown.

The figures are schematic in nature and are merely intended to aid understanding of the disclosure. Identical elements are provided with the same reference signs. The features of the various configuration examples can be interchanged.

DETAILED DESCRIPTION OF PREFERRED EMBODIMENTS

Figure 1:
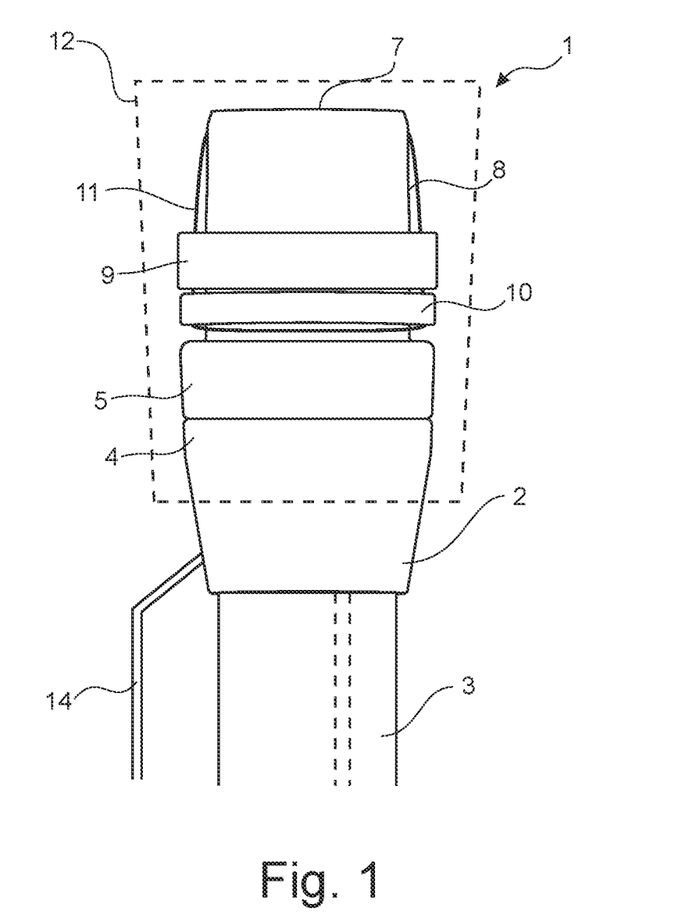
FIG. 1 shows a schematic view of a tissue-clip application fitting or retrofitting set fixed to an endoscope according to a preferred configuration example.

FIG. 1 shows a schematic view of a tissue-clip application fitting or retrofitting set 1, which is configured as a cap attachment 2 or has a cap attachment 2. The cap attachment 2 may be placed on a distal end portion (endoscope head) of an endoscope 3, may in particular be attached or slipped on. The endoscope 3 shown only in part in FIG. 1, as is known from the prior art mentioned above and the description of which is also made the subject matter of this application, generally has a (flexible or rigid) endoscope shaft, at the distal end of which at least one optical system and an illumination device are installed. Furthermore, such an endoscope 3 often has an internal working channel through which a (minimally invasive) medical instrument (e.g., forceps, scissors, and the like) is insertable into a cavity of a patient, for example (shown in dashed lines or indicated in FIG. 1). Finally, a rinsing device may be provided at the distal end (endoscope head) of the endoscope 3 via which the optics can be cleaned.

At its proximal end portion, the endoscope 3 of known design also has an endoscope handle on which the endoscope 3 can be held and operated. It should be noted at this point that the endoscope 3 may also have an interface to a robot instead of a handle.

The tissue-clip application fitting or retrofitting set 1 or the cap attachment 2 according to the preferred configuration example has a proximal mounting/placement portion 4 and a distal tissue-clip holding portion 5, wherein both portions may also overlap axially at least partially or completely. As mentioned above, the tissue-clip application fitting or retrofitting set 1 with its mounting/placement portion 4 may be temporarily mounted or respectively slipped onto the distal end portion of the endoscope 3. For this purpose, the mounting/placement portion 4 is preferably formed in the form of a sleeve or cuff made of a flexible, preferably elastic, material. Alternatively, it is also possible to manufacture the mounting/placement portion 4 from a plastic sleeve which can be radially expanded, e.g. by arranging at least one longitudinal slot or as a result of a predetermined inherent flexibility. Furthermore, the mounting/placement portion 4 is provided to be slipped onto the distal end portion, i.e. in particular not to be inserted into the internal working channel of the endoscope 3, so as to form a quasi axial extension of the distal end portion of the endoscope shaft. The internal working channel of the endoscope 3 thus remains open and usable for the insertion of a medical instrument.

At this point, it should be mentioned that the cap attachment 2 can also be coupled to the endoscope head of the (commercially available) endoscope 3 in another way, for example via a separate cap sleeve, a heat shrink tube and similar connecting elements.

The tissue-clip holding portion 5 consists of a plastic sleeve which is preferably more rigid (hollow) than the mounting/placement portion 4 and which is preferably connected to the mounting/placement portion 4 as an extension thereof in one piece, in particular in one piece of material, or is coupled to the mounting/placement portion 4, for example by bonding or welding. At least the tissue-clip holding portion 5 forms a hollow or cavity 6 on the inside, which is provided, for example, for temporarily receiving patient tissue and which merges at the distal end of the tissue-clip holding portion 5, forming a distal front or end edge 7, into a lateral surface/outer peripheral surface 8 pointing radially outwards, on which a tissue clip 9 (in the expanded state) is supported so that it is axially movable.

It should be noted at this point that this outer peripheral surface 8 may be the maximum radially outer surface (as shown in FIG. 1) or may again be covered/surrounded by a peripheral surface arranged radially further out, forming an axially extending annular gap to receive the tissue clip 9 (not shown in FIG. 1).

As can be seen in FIG. 1, the tissue clip 9 is connected/attached at its proximal front side/edge to a pull-off ring 10 also supported/mounted on the outer peripheral surface 8 of the tissue-clip holding portion 5. The pull-off ring 10 is thereby coupled to a pull-off string 11 in such a way that, as described in more detail below and shown in FIG. 2, when the pull-off string 11 is manually actuated (pulling the pull-off string 11 in the proximal direction), the pull-off ring 10 slides along the tissue-clip holding portion 5 in the distal direction, thereby shifting/displacing the tissue clip 9 in the distal direction. In other words, the pull-off ring 10 and thus also the tissue clip 9 are displaced in the axial direction of the tissue-clip holding portion 5 when the pull-off string 11 is pulled.

As indicated in FIG. 1, a cap sleeve 12 may be arranged/fixed to the cap attachment 2 or the cap sleeve 12 may be firmly connected, in particular in one piece of material with the cap attachment 2. This cap sleeve 12 surrounds the tissue clip 9, which is pulled onto the tissue-clip holding portion 5, at least in sections, and thus enables at least partial shielding of the pull-off device consisting of pull-off ring 10 and pull-off string 11.

Figure 3:
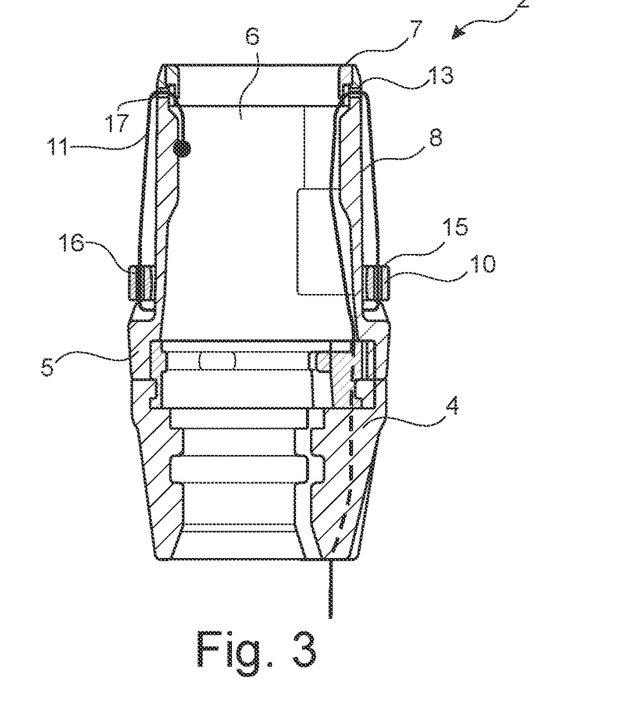
FIG. 3 shows a longitudinal sectional view of the tissue-clip application fitting or retrofitting set according to a modification of the preferred configuration example.

FIG. 3 shows a longitudinal cross-section of the tissue-clip application fitting or retrofitting set 1 according to the preferred configuration example.

In a distal end region (facing away from the user) of the tissue-clip holding portion 5, a first radial through opening 13 is configured, which connects the inner cavity 6 with the outer peripheral surface 8 and through which the pull-off string 11 guided in the cavity 6 is guided. In the preferred configuration example, the pull-off string 11 extends with its proximal end portion through the cavity 6 towards the endoscope 3 and is guided through a separate longitudinal passage 14 temporarily arranged on the endoscope 3, for example with clips and/or straps, up to the proximal end portion of the endoscope 3, i.e. preferably out of the hollow organ of the patient, so that the pull-off string 11 can be operated/actuated from outside the hollow organ of the patient, preferably manually. Alternatively, the pull-off string 11 may also be guided via the cavity 6 into the working channel of the endoscope 3 and there up to the proximal end portion of the endoscope 3. As a further alternative, it is also possible to guide the pull-off string in a tube/channel held separately from the endoscope/endoscope shaft, whereby the cap attachment together with the attached clip, the tube and the pull-off string guided longitudinally therein form the uniform tissue-clip application fitting or retrofitting set 1, which can be added to the (commercially available) endoscope as an optional smart function without impairing its internal functions.

In the preferred configuration example, the pull-off string 11, as described above, is guided through the first radial through opening 13 starting from the cavity 6 radially onto the outer/peripheral surface of the tissue clip application fitting or retrofitting set 1, from where it is guided proximally through a first axial through opening 15 formed in the pull-off ring 10. Subsequently, as shown in FIG. 2, the pull-off string 10 runs along the outer peripheral surface 8 of the (sleeve-shaped) cap attachment 2 around the tissue-clip holding portion 5 (i.e. in the circumferential direction), before it is guided through a second axial through opening 16 formed in the pull-off ring 10, preferably offset by 180° with respect to the first axial through opening 15, in the direction distal to the distal end region of the tissue-clip holding portion 5, where it is returned through a second radial through opening 17, preferably offset by 180° with respect to the first radial through opening 13, into the cavity 6 in order to be fastened (there) to the tissue-clip holding portion 5.

In other words, one end of the pull-off string 11 is attached to the proximal end portion of the endoscope 3 and the other end of the pull-off string 11 is attached to the tissue-clip holding portion 5 as shown in FIG. 3. Starting from the proximal end portion of the endoscope 3, the pull-off string 11 is guided through the separate channel or the working channel (tube) or through a channel of the endoscope 3 towards its distal end portion and there into the cavity 6 of the tissue-clip application fitting or retrofitting set 1. At the distal end region of the tissue-clip holding portion 5, the pull-off string 11 passes through the first radial through opening 13 to the outside, where it is guided proximally along the outer peripheral surface 8, through the first axial through opening 15 of the pull-off ring 10 and thereafter along the outer peripheral surface 8 and through the second axial through opening 16 of the pull-off ring 10 again in the distal direction. Through the second radial through opening 17 formed at the distal end region of the tissue-clip holding portion 5, the pull-off string 11 re-enters the cavity 6 to be attached to the tissue-clip holding portion 5.

This string guiding essentially corresponds to a simple pulley with a firmly fixed upper string end, an (actuating) end that is initially guided around an upper deflection and then extends downward, and a string center portion that is located between the fixation and deflection and is looped into a load.

Figure 2:
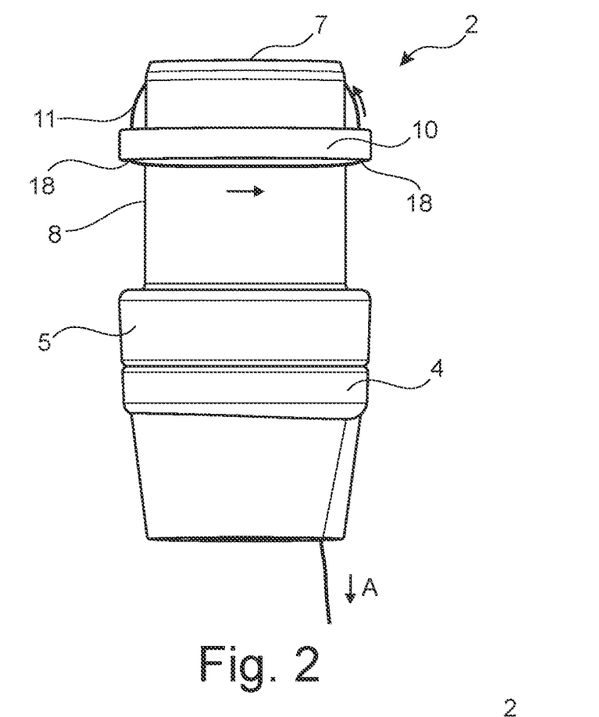
FIG. 2 shows a side view of the tissue-clip application fitting or retrofitting set according to the preferred configuration example.

If a user now actuates the pull-off string 11 at the proximal end portion of the endoscope 3, i.e. pulls the pull-off string 11 in the proximal direction, as shown by the arrow A in FIG. 2, an axial force acts on the pull-off ring 10 at least at two engagement points 18 in the region of the two axial through openings 15, 16 in the distal direction, which finally shifts/displaces the pull-off ring 10 towards the distal end portion of the tissue-clip holding portion 5 in order to strip the tissue clip 9 from the tissue-clip holding portion 5 over its front edge 7. Since an axial force acts on the pull-off ring 10 at least at each of the two engagement points 18, any tilting moment occurring at only one engagement point when an axial force is applied, which tilts/twists the pull-off ring 10 relative to its central axis/axis of rotation, can be eliminated or at least minimized, which in turn reduces the risk of jamming of the pull-off ring 10 on the tissue-clip holding portion 5.

In other words, the function of the tissue-clip application fitting or retrofitting set 1 according to the preferred configuration example or the modification of the preferred configuration example can generally be described as follows: First, the tissue-clip application fitting or retrofitting set 1 according to the disclosure is attached/slipped onto the distal end portion of the (generally known) endoscope 3. The distal end portion of the endoscope 3, together with the tissue-clip application fitting or retrofitting set 1 slipped onto it, can be oriented towards a wall of a hollow organ via a known orientation mechanism, e.g. in the form of Bowden cables. As soon as the tissue-clip application fitting or retrofitting set 1 is pressed against the tissue of the hollow organ wall of the patient on the distal front side, i.e. with its distal front edge 7 (which may be rounded), the patient tissue can be drawn into the cavity 6 of the tissue clip application fitting or retrofitting set 1. This is done via negative pressure built up in the cavity 6 and/or via an inserted instrument (forceps, hook, tissue anchor, etc.). In addition, another medical instrument can be introduced into the cavity 6 via the inner working channel of the endoscope 3 in order to grasp the patient tissue to be treated at two locations that are spaced apart from each other and to pull it into the cavity 6. In this way, the patient tissue can be gripped more easily. As soon as sufficient tissue has been drawn into the cavity 6, the tissue clip 9 is stripped off in the distal direction via the pull-off string 11 over the front edge 7, wherein the latter then clamps the patient tissue together.

Figure 4:
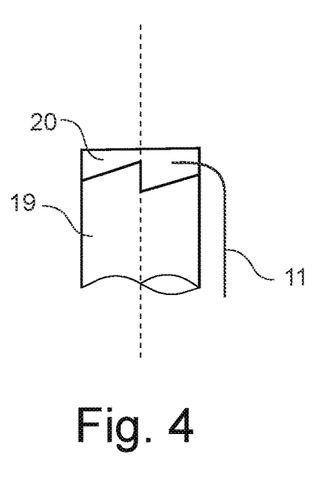
FIGS. 4-6 show schematic partial views of a pull-off device according to a further configuration example, which may be claimed independently, if applicable.
Figure 5:
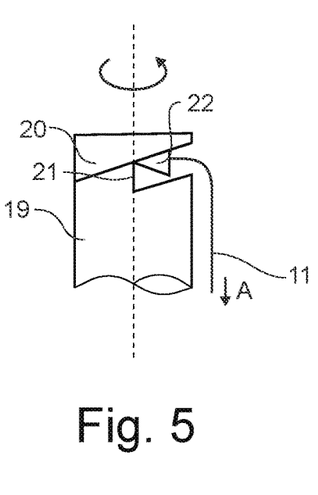
Figure 6:
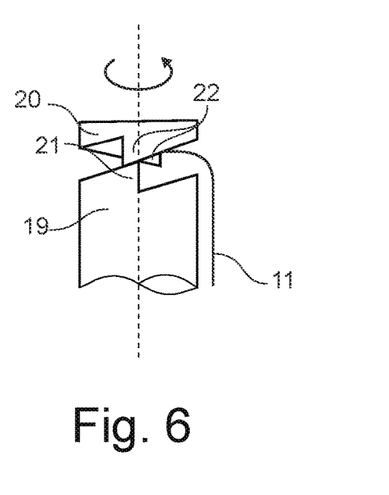

FIGS. 4 to 6 schematically show a pull-off device according to an alternative configuration example, which may be claimed independently of the above configuration example, wherein in the following essentially only the features different from the first configuration example will be discussed.

The pull-off ring 10 is therefore made in two parts and has a stationary support ring/connecting piece 19 connected to the cap attachment 2 and a sliding-rotating ring 20 (hereinafter referred to only as sliding ring) that can be displaced relative to the support ring 19. The pull-off string 11 is attached to an outer peripheral surface of the sliding ring 20 in such a way that the pull-off string 11 extends at least in sections in the circumferential direction, so that the sliding ring 20 is rotated about its axis of rotation when the pull-off string 11 is actuated, i.e. when the pull-off string 11 is pulled in the proximal direction.

As can be seen in FIG. 4, the front face of the support ring 19 facing the sliding ring 20 is configured with two ramps/cams/wedge profiles 21. In addition, the front face of the sliding ring 20 facing the support ring 19 also has two ramps 22 running in opposite directions to the wedge profiles 21. That is, the respective end faces of the support ring 19 or of the sliding ring 20 are configured with ramp surfaces/profiles in such a way that the ramp surfaces/profiles, preferably the ramps 21, 22, slide against each other when the sliding ring 20 rotates relative to the support ring 19 and thus increasingly space the sliding ring 20 and the support ring 19 axially away from each other, as indicated in FIGS. 5 and 6. The sliding ring 20 pushes the tissue clip 9 in the distal direction in order to strip it from the tissue clip holding portion 5.

In the preferred configuration example described above, the pull-off string 11 is guided between the outer peripheral surface 8 and the tissue clip 9. That is, the pull-off string 11 runs between the first radial through opening 13 and the first axial through opening 15 and between the second axial through opening 16 and the second radial through opening 17 radially inwards past the tissue clip 9. It is also conceivable to configure a respective axial groove on the outer peripheral surface 8 of the tissue clip holding portion 5 in which the pull-off string 11 is guided, so that the tissue clip 9 brushes over the pull-off string 11 guided in the axial grooves during stripping.

Furthermore, in the preferred configuration example, a pull-off string 11 is guided along the cap attachment 2 such that the two engagement points 18 are set when actuated.

Alternatively, however, the pull-off string 11 may also be guided along the cap attachment 2 in such a way that more than two engagement points are configured. This means that the pull-off string 11 is guided through further radial through openings and axial through openings in order to obtain additional engagement points. However, as with a pulley, a deflection point has to be arranged or configured distally between the engagement points. In order to configure the deflection point, the pull-off string 11 may, for example, be guided over the front edge 7 inwards into the cavity 6, through a further, distal radial through opening outwards again and there to the next proximal engagement point on the pull-off ring 10.

Also, in the preferred configuration example, the pull-off string 11 is fixed to the cap attachment 2 internally in the region of the cavity 6. However, another fixation site is also conceivable as long as the pull-off string 11 is distally held in a stationary manner. Thus, the pull-off string 11 may be fixed distally to the outer peripheral surface 8 or may have, at its distal end, a body or node with a cross-sectional area larger than the cross-sectional area of the second radial through opening 17, which is configured or attached after the second radial through opening 17 has been passed through, so that the distal end of the pull-off string 11 can no longer slip through the second radial through opening 17 or is held stationary.

Furthermore, in the preferred configuration example, the pull-off string 11 is guided at the engagement points through the axial through openings. However, it is also conceivable that eyelets are configured or arranged on the pull-off ring 10 to deflect the pull-off string 11.

As mentioned above, in the preferred configuration example, two engagement points 18 are formed on the pull-off ring 10 due to the guidance of the pull-off string 11. However, as an alternative to configuring the two engagement points, a second pull-off string may be arranged or respectively a plurality of pull-off strings for a plurality of engagement points. In other words, a separate pull-off string may be associated with each engagement point.

Furthermore, in the further configuration example, the support ring 19 and the sliding ring 20 have ramps 21, 22. Alternatively, an internal thread may be configured on the support ring 19, which engages with an external thread configured on the sliding ring 20, so that upon rotation of the sliding ring 20 due to actuation of the pull-off string 11, the sliding ring 20 is displaced in the distal direction relative to the support ring 19. It is of course also conceivable that the internal thread is configured on the sliding ring 20 and the external thread on the support ring 19.

LIST OF REFERENCE SIGNS

1 tissue-clip application fitting or retrofitting set
2 cap attachment
3 endoscope
4 mounting/placement portion
5 tissue-clip holding portion
6 cavity
7 front edge
8 lateral surface/outer peripheral surface
9 tissue clip
10 pull-off ring
11 pull-off string
12 cap sleeve
13 first radial through opening
14 longitudinal passage
15 first axial through opening
16 second axial through opening
17 second radial through opening
18 engagement point
19 support ring
20 sliding ring
21 support-ring side ramp/cam
22 sliding-ring side ramp/cam

The invention claimed is:

1. A tissue-clip application fitting or retrofitting cap attachment for mounting on a distal end portion of a medical endoscope of a shaft type, the cap attachment comprising:
    a mounting or placement portion configured to be mounted on the distal end portion of the medical endoscope; and
    a tissue-clip holding portion having:
    an internal cavity, which is open at least in a distal direction extending away from the mounting or placement portion,
    a peripheral surface surrounding the internal cavity and facing radially outwards from the internal cavity,
    a tissue clip radially supported on the peripheral surface, and axially slidable along the peripheral surface in the distal direction,
    a pull-off ring axially slidably mounted on the peripheral surface,
    and a pull-off string configured to actuate the pull-off ring to move the pull-off ring and the tissue clip in the distal direction, wherein the pull-off ring string is directly in sliding-force introduction contact with the pull-off ring in at least two engagement points.

2. The tissue-clip application fitting or retrofitting cap attachment according to claim 1, wherein the at least two engagement points are evenly distributed about the peripheral surface.

3. The tissue-clip application fitting or retrofitting cap attachment according to claim 2, wherein the pull-off string has:
    a first end fixed to a portion of the cap attachment;
    a first portion extending from the first end to the pull-off ring at a first one of the at two engagement points;
    a second portion extending from the first one of the at least two engagement points to the pull-off ring at a second one of the at least two engagement points; and
    a third portion extending from the second one of the at least two engagement points around a distal end portion of the cap attachment, and then in a proximal direction opposite the distal direction to a proximal end portion of the endoscope.

4. The tissue-clip application fitting or retrofitting cap attachment according to claim 3, wherein the pull-off string is slidably guided longitudinally between the first one of the at least two engagement points and the second one of the at least two engagement points on the peripheral surface of the cap attachment in such a way that, when the pull-off string is actuated, it pulls the pull-off ring in a pulley-like manner in the distal direction at the at least two engagement points.

5. The tissue-clip application fitting or retrofitting cap attachment according to claim 4, wherein the pull-off string is in sliding contact with a proximal front face of the pull-off ring in a circumferential section of the pull-off ring between the first one of the at least two engagement points and the second one of the at least two engagement points.

6. The tissue-clip application fitting or retrofitting cap attachment according to claim 3, wherein:
    the first end of the pull-off string is located inside the cavity;

the pull-off string extends from the first end through a first distal radial through opening formed in the tissue-clip holding portion from the cavity to the peripheral surface;

the pull-off string extends from the first distal radial through opening and then through a first axial through opening formed in the pull-off ring at the first one of the at least two engagement points;

the pull-off string extends from the first axial through opening and then through a second axial through opening formed in the pull-off ring at the second one of the at least two engagement points; and the pull-off string extends from the second axial through opening and then through a second distal radial through opening formed in the tissue-clip holding portion from the peripheral surface to the cavity.

\* \* \* \* \*

UNITED STATES PATENT AND TRADEMARK OFFICE
CERTIFICATE OF CORRECTION

| | | |
|---|---|---|
| PATENT NO. | : 12,343,018 B2 | Page 1 of 1 |
| APPLICATION NO. | : 17/925511 | |
| DATED | : July 1, 2025 | |
| INVENTOR(S) | : Marcus Braun | |

It is certified that error appears in the above-identified patent and that said Letters Patent is hereby corrected as shown below:

In the Claims

Column 10, Line 28, Claim 1, delete "pull-off ring string" and insert -- pull-off string --

Signed and Sealed this
Second Day of September, 2025

Coke Morgan Stewart
*Acting Director of the United States Patent and Trademark Office*